United States Patent
Nishiyama et al.

(10) Patent No.: US 11,465,128 B2
(45) Date of Patent: Oct. 11, 2022

(54) CATALYST, METHOD FOR PRODUCING SAME, AND METHOD FOR PRODUCING DIENE COMPOUND USING SAID CATALYST

(71) Applicant: SEKISUI CHEMICAL CO., LTD., Osaka (JP)

(72) Inventors: Haruka Nishiyama, Tsukuba (JP); Noritoshi Yagihashi, Tsukuba (JP); Toshihito Miyama, Tsukuba (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 16/770,743

(22) PCT Filed: Jan. 10, 2019

(86) PCT No.: PCT/JP2019/000482
§ 371 (c)(1),
(2) Date: Jun. 8, 2020

(87) PCT Pub. No.: WO2019/139071
PCT Pub. Date: Jul. 18, 2019

(65) Prior Publication Data
US 2021/0170364 A1    Jun. 10, 2021

(30) Foreign Application Priority Data
Jan. 12, 2018 (JP) .............................. JP2018-003731

(51) Int. Cl.
*B01J 21/06* (2006.01)
*B01J 21/08* (2006.01)
(Continued)

(52) U.S. Cl.
CPC ............. *B01J 21/066* (2013.01); *B01J 21/08* (2013.01); *B01J 37/024* (2013.01);
(Continued)

(58) Field of Classification Search
CPC ...... B01J 21/066; B01J 21/08; B01J 37/0205; B01J 37/024; B01J 37/088; C07C 1/24; C07C 2521/06; C07C 2521/08
See application file for complete search history.

(56) References Cited

U.S. PATENT DOCUMENTS 6,083,347 A * 7/2000 Thebrin .................. A61L 15/18
162/181.1
9,233,360 B1 * 1/2016 Jothimurugesan ... B01J 37/0207
(Continued)

FOREIGN PATENT DOCUMENTS

CN    106861752    6/2017
JP    59-62346     4/1984
(Continued)

OTHER PUBLICATIONS

Moreau, J. et al. (2012) Langmuir, 29, 207-215.*
(Continued)

*Primary Examiner* — Brian A McCaig
(74) *Attorney, Agent, or Firm* — Wenderoth, Lind & Ponack, L.L.P.

(57) ABSTRACT

The present invention relates to a catalyst including: a porous carrier including at least one element X selected from the group consisting of elements belonging to Groups 13 and 14 of the periodic table; an oxide of at least one metal element A selected from the group consisting of elements belonging to Groups 3 to 6 of the periodic table; and at least one oxide of a metal element B selected from the group consisting of elements belonging to Group 2 and Groups 7 to 12 of the periodic table, wherein at least a part of the oxide of the metal element A is bonded to the porous carrier.

10 Claims, 1 Drawing Sheet

(51) Int. Cl.
    *B01J 37/02*     (2006.01)
    *B01J 37/08*     (2006.01)
    *C07C 1/24*     (2006.01)

(52) U.S. Cl.
    CPC ......... *B01J 37/0205* (2013.01); *B01J 37/088* (2013.01); *C07C 1/24* (2013.01); *C07C 2521/06* (2013.01); *C07C 2521/08* (2013.01)

(56) References Cited

U.S. PATENT DOCUMENTS

| | | | |
|---|---|---|---|
| 10,207,253 B1* | 2/2019 | Inokawa | C07C 45/38 |
| 2007/0260075 A1* | 11/2007 | Jubin, Jr. | C07D 301/04 |
| | | | 549/533 |
| 2016/0082417 A1 | 3/2016 | Lewandowski et al. | |
| 2016/0228851 A1* | 8/2016 | Hermans | B01J 23/30 |
| 2017/0260112 A1 | 9/2017 | Nishino et al. | |
| 2017/0349503 A1* | 12/2017 | Chinta | C07C 45/002 |
| 2018/0200696 A1 | 7/2018 | Cadran et al. | |

FOREIGN PATENT DOCUMENTS

| | | |
|---|---|---|
| JP | 2015-168644 | 9/2015 |
| JP | 2016-23141 | 2/2016 |
| JP | 2016-518395 | 6/2016 |
| KR | 10-2014-0050531 | 4/2014 |
| WO | 2014/129248 | 8/2014 |
| WO | 2014/199349 | 12/2014 |
| WO | 2016/043209 | 3/2016 |
| WO | 2017/009108 | 1/2017 |

OTHER PUBLICATIONS

Julian, J.R.H. (2012) Heterogeneous Catalysis: Fundamentals and Applications, 1st edition, Elsevier, 232 pp [Office action cites p. 84].*

Murzin, D. (2013) Engineering Catalysis, De Gruyter, 376 pp [Office action cites pp. 143-144].*

International Search Report dated Mar. 5, 2019 in International (PCT) Application No. PCT/JP2019/000482.

Gutierrez et al., "DeepHDS over NiMo/Zr—SBA-15 catalysts with varying $MoO_3$ loading", Catalysis Today, vol. 130, 2008, pp. 292-301.

Pomalaza et al., "Recent Breakthroughs in the Conversion of Ethanol to Butadiene", catalysts, 2016, vol. 6, No. 203, pp. 1-35.

Baerdemaeker et al., "Bimetallic Zn and Hf on Silica Catalysts for the Conversion of Ethanol to 1,3-Butadiene", ACS Catalysis, vol. 5, 2015, pp. 3393-3397.

Extended European Search Report dated Sep. 6, 2021 in corresponding European Patent Application No. 19738363.1.

* cited by examiner

CATALYST, METHOD FOR PRODUCING SAME, AND METHOD FOR PRODUCING DIENE COMPOUND USING SAID CATALYST

TECHNICAL FIELD

The present invention relates to a catalyst, a method for producing the same, and a method for producing a diene compound using the catalyst.

Priority is claimed on Japanese Patent Application No. 2018-003731, filed on Jan. 12, 2018, the content of which is incorporated herein by reference.

BACKGROUND ART

Butadiene such as 1,3-butadiene, which is a representative example of diene compounds, is used as a raw material for styrene-butadiene rubber (SBR) and the like. Conventionally, butadiene has been purified from the C4 fraction. The C4 fraction is a fraction obtained as a by-product in naphtha cracking for producing ethylene from petroleum. However, the use of petroleum has decreased as a result of increased use of shale gas. Consequently, the butadiene production by naphtha cracking of petroleum has also decreased. Therefore, there is a demand for an alternative method for producing diene compounds such as 1,3-butadiene.

For example, Patent Document 1 discloses an invention relating to a metal-impregnated silica catalyst for selectively converting ethanol into butadiene. More specifically, Patent Document 1 describes a butadiene synthesis catalyst including Hf and two or more catalytically active metals M1 and M2, wherein the two or more catalytically active metals M1 and M2 are selected from the group consisting of Zr, Zn, Cu, and combinations thereof, provided that M1 and M2 are different.

Patent Document 1 describes a method for synthesizing butadiene, which includes (i) providing a gas stream G-1 containing ethanol and optional acetaldehyde, and (ii) contacting the gas stream G-1 with the butadiene synthesis catalyst to obtain a gas stream G-2 containing butadiene.

Patent Document 1 describes that the method for synthesizing butadiene achieves a butadiene selectivity of at least 10%.

DESCRIPTION OF PRIOR ART

Patent Document
Patent Document 1: International Patent Application Publication No. 2014/199349

DISCLOSURE OF INVENTION

Problems to be Solved by the Invention

Although the invention described in Patent Document 1 enables butadiene synthesis using ethanol as a raw material gas, it is necessary to reduce the ethanol concentration in the raw material gas. For this reason, according to the invention described in Patent Document 1, the yield of butadiene per unit time is low, and it is difficult to increase the production efficiency of butadiene.

In this situation, the object of the present invention is to provide a catalyst that can efficiently produce a diene compound even when the alcohol concentration in the raw material gas is high.

Means to Solve the Problems

The present inventors have made intensively studies to solve the above-mentioned problems. As a result, they have found that the above problems can be solved by a catalyst obtained by contacting an oxide containing specific metals with a porous carrier, and have completed the present invention.

That is, the embodiments of the present invention are as follows.

[1] A catalyst including:
a porous carrier including at least one element X selected from the group consisting of elements belonging to Groups 13 and 14 of the periodic table;
an oxide of at least one metal element A selected from the group consisting of elements belonging to Groups 3 to 6 of the periodic table; and
at least one oxide of a metal element B selected from the group consisting of elements belonging to Group 2 and Groups 7 to 12 of the periodic table, wherein at least a part of the oxide of the metal element A is bonded to the porous carrier.

[2] The catalyst according to [1], wherein a ratio of the number of moles of the metal element A to the number of moles of the element X (metal element A/element X) is 0.001 to 1.

[3] The catalyst according to [1] or [2], wherein a ratio of the number of moles of the metal element B to the number of moles of the element A (metal element B/element A) is 0.1 to 10.

[4] The catalyst according to any one of [1] to [3], wherein the porous carrier has mesopores.

[5] The catalyst according to any one of [1] to [4], which is a catalyst for synthesizing a diene compound from a raw material gas containing an alcohol.

[6] The catalyst according to [5], wherein the raw material gas is ethanol, or a mixture of ethanol and acetaldehyde.

[7] A method for producing the catalyst of any one of [1] to [6], comprising:
reacting a compound containing the metal element A with the porous carrier to prepare a catalyst precursor in which at least a part of the oxide of the metal element A is bonded to the porous carrier; and
reacting the catalyst precursor with a compound containing the metal element B.

[8] The method according to [7], wherein the catalyst precursor is prepared by a method including:
impregnating a porous carrier with a first solution containing a compound containing the metal element A to obtain a solution containing an impregnated product; and
separating the impregnated product from the first solution; and
calcining the impregnated product.

[9] A method for producing a diene compound, including contacting the catalyst of any one of [1] to [6] with a raw material gas containing an alcohol to obtain a diene compound.

[10] The method according to [9], wherein a reaction temperature for obtaining the diene compound is 200 to 600° C.

Effect of the Invention

The catalyst of the present invention enables efficient production of a diene compound even when the alcohol concentration in the raw material gas is high.

DESCRIPTION OF THE EMBODIMENTS

Figure 1:
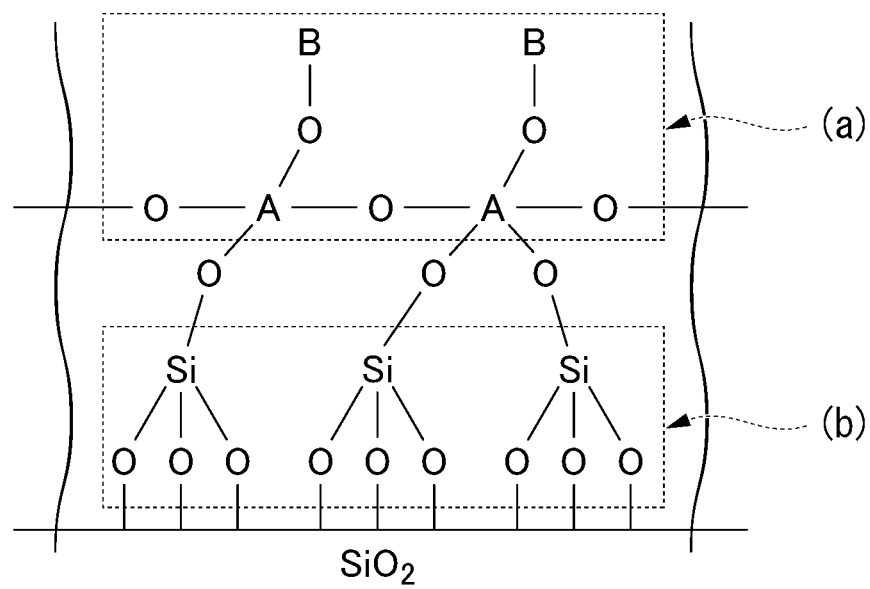
FIG. 1 is a schematic view of a catalyst according to one embodiment of the present invention.
Figure 2:
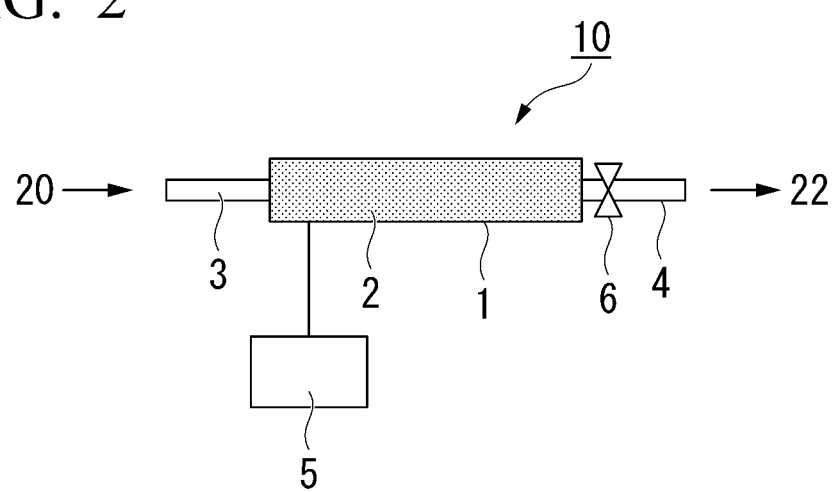
FIG. 2 is a schematic view of an apparatus for producing butadiene according to one embodiment of the present invention.

Hereinbelow, embodiments of the present invention are described in detail, but the following descriptions illustrate only examples of the embodiments of the present invention, and the present invention is not limited thereto and may be modified as long as the modifications do not deviate from the gist of the present invention.

<Catalyst>

The catalyst of the present embodiment includes: a porous carrier including at least one element X selected from the group consisting of elements belonging to Groups 13 and 14 of the periodic table; an oxide of at least one metal element A selected from the group consisting of elements belonging to Groups 3 to 6 of the periodic table; and at least one oxide of a metal element B selected from the group consisting of elements belonging to Group 2 and Groups 7 to 12 of the periodic table. In this catalyst, at least a part of the oxide of the metal element A is bonded to the porous carrier.

The catalyst enables efficient production of a diene compound even when the alcohol concentration in the raw material gas is high.

More specifically, when the alcohol is converted into a diene compound, usually the alcohol first reacts with the oxide of the metal element B and then reacts with the oxide of the metal element A.

Since the oxide of the metal element B is bonded to the porous carrier or the metal element A, the oxide of the metal element B is primarily disposed on the outermost surface of the catalyst. This increases the chance of contact between the alcohol the oxide of the metal element B, which allows the reaction to proceed efficiently, thereby improving the conversion.

On the other hand, when the alcohol reacts with the oxide of the metal element A, a by-product such as ethylene may be generated. However, at least a part of the oxide of the metal element A is bonded to the porous carrier. That is, the oxide of the metal element A is disposed close to the porous support (disposed inside the catalyst), and the alcohol is allowed little or no chance of contact with the oxide of the metal element A, whereby the generation of by-products can be prevented or suppressed, and the selectivity for the diene compound can be improved.

Further, since the oxide of the metal element A is bonded to the oxide of the metal element B in at least a part of the catalyst, both oxides are positioned close to each other. For this reason, the alcohol reacts with the oxide of the metal element B, and the resulting product easily reacts with the oxide of the metal element A. Thus, the conversion of the diene compound from the alcohol is efficiently performed, so that the selectivity for the diene compound and the conversion can be improved.

Further, at least a part of the oxide of the metal element A is bonded to the porous carrier. This allows the oxide of the metal element A to be dispersed in the catalyst. That is, in principle, the catalyst does not have a morphology in which the bond between the oxide of the metal element A and another oxide of the metal element A is arranged toward the outermost surface. Therefore, it is possible to prevent or suppress the generation of by-products caused by the local presence of the oxide of the metal element A having high reaction activity, and to improve the selectivity for the diene compound.

The mechanism described above is based only on a presumption, and even if the effect of the present invention can be obtained through another mechanism, it is included in the technical scope of the present invention.

[Porous Carrier]

The porous carrier contains at least one element X selected from the group consisting of elements belonging to Groups 13 and 14 of the periodic table.

Examples of the element X include elements belonging to Group 13 of the periodic table, such as aluminum, gallium, and indium; and elements belonging to Group 14 of the periodic table, such as silicon and germanium. Among these, the element X is preferably aluminum or silicon, and more preferably silicon.

Further, the porous carrier may further include elements belonging to Group 1 and Group 2 of the periodic table, oxygen, and the like.

Examples of the Group 1 element include sodium, potassium, rubidium, cesium and the like.

Examples of the Group 2 element include beryllium, magnesium, calcium, strontium, barium and the like.

Examples of the porous carrier include silica, alumina, and zeolite (e.g., zeolites with structure codes LTA, FER, MWW, MFI, MOR, LTL, FAU, BEA, and the like). Among these, it is preferable to use silica.

The silica is preferably a mesoporous silica having mesopores.

One of the porous carriers described above may be used alone, or two or more thereof may be used in combination.

The porous carrier preferably has mesopores. In this specification, the porous carrier having mesopores means that the carrier is porous with an average pore diameter of 2 to 50 nm, preferably 2 to 30 nm, and more preferably 2 to 15 nm. The average pore diameter of not less than 2 nm is favorable in that the diffusivity of the alcohol is improved, and the raw material conversion and the diene compound selectivity are further increased. On the other hand, the average pore diameter of not more than 50 nm is favorable in that the contact area between the alcohol and the catalyst increases, so that the raw material conversion and the butadiene selectivity are further increased. The "average pore diameter" is a value measured by the following method. That is, the average pore diameter is calculated from the total pore volume (total of the pore volumes of the catalyst) and the BET specific surface area. Specifically, the average pore diameter can be calculated on the assumption that the pores are in the form of a cylinder (BJH method). With the BET specific surface area $A1$ being used as the side area of the cylinder and the total pore volume $V1$ being used as the volume of the cylinder, the average pore diameter can be calculated by $4V1/A1$.

The total pore volume of the porous carrier is preferably 0.1 to 10.0 mL/g, more preferably 0.1 to 5.0 mL/g, and even more preferably 0.1 to 2.0 mL/g. The total pore volume of not less than 0.1 mL/g is favorable in that the diffusibility of the alcohol is improved, and the raw material conversion and the diene compound selectivity are further increased. On the other hand, the total pore volume of not more than 10.0 mL/g is favorable in that the contact area between the alcohol and the catalyst increases, so that the raw material conversion and the butadiene selectivity are further increased. In the present specification, the "total pore volume" of the catalyst is a value measured by a gas adsorption method. The gas adsorption method is a method in which nitrogen gas is used as an adsorption gas, nitrogen molecules are allowed to be adsorbed on the surface of the synthesis catalyst, and pore distribution is measured from condensation of the molecules.

The specific surface area of the porous carrier is preferably 100 to 5000 $m^2/g$, and more preferably 500 to 2000 $m^2/g$. The specific surface area of not less than 100 $m^2/g$ is favorable in that a sufficient amount of the catalyst components can be supported on the surface of the porous carrier, so that the raw material conversion and the diene compound selectivity are further increased. As a result, the raw material conversion is increased even when the alcohol content is high with respect to 100% by volume of the raw material gas (in terms of gas volume). For example, a high raw material conversion is achieved even with the alcohol content of 100% by volume. On the other hand, the specific surface area of not more than 5000 $m^2/g$ is favorable in that the contact area between the alcohol and the catalyst increases, and the raw material conversion and the diene compound selectivity are further increased. In the present specification, the specific surface area means the BET specific surface area, which is measured by the BET gas adsorption method using nitrogen as an adsorption gas.

The product of the total pore volume times the specific surface area of the porous carrier is preferably 10 to 50000 $mL \cdot m^2/g^2$, more preferably 20 to 25000 $mL \cdot m^2/g^2$, even more preferably 20 to 2000 $mL \cdot m^2/g^2$. The product of not less than 10 $m L \cdot m^2/g^2$ is favorable in that a sufficient amount of the catalyst components can be supported on the surface of the porous carrier, and the diffusivity of the raw material gas containing an alcohol is improved, thereby allowing for further increase in the raw material conversion and the diene compound selectivity. On the other hand, the product of not more than 50000 $mL \cdot m^2/g^2$ is favorable in that the contact area between the alcohol and the catalyst tends to be sufficient, and the raw material conversion and the diene compound selectivity are further increased.

The mesopore volume ratio (total mesopore volume/total pore volume×100) of the porous carrier is preferably 50% or more, more preferably 50 to 100%, even more preferably 80 to 100%, and particularly preferably 90 to 100%. The mesopore volume ratio of 50% or more is favorable in that a sufficient amount of mesopores are provided in the catalyst and the diffusivity of the raw material gas containing an alcohol is improved, thereby allowing for further increase in the raw material conversion and the diene compound selectivity.

The shape of the mesopores is not particularly limited, and examples thereof include a two-dimensional hexagonal structure, a three-dimensional hexagonal structure, a cubic structure, and a layered structure.

Further, the pore walls forming the mesopores preferably have a crystal structure. The shape of the mesopores and whether or not the pore walls forming the mesopores have a crystal structure can be determined by observing a diffraction peak obtained by X-ray diffractometry. Specifically, when the pore walls forming the mesopores have a crystal structure, a peak ascribed to the periodic structure of the mesopores is observed at a low angle of $2\theta=1$ to $6°$ in the X-ray diffraction pattern. The shape and regularity of the mesopores can be determined by observing the catalyst with a transmission electron microscope (TEM).

The molar amount of the element X may be 50 to 99 mol %, more preferably 60 to 99 mol %, and even more preferably 70 to 99 mol %, with the proviso that the sum of the molar ratio of the element X, the molar ratio of the metal element A, and the molar ratio of the metal element B in the catalyst is 100 mol %.

The mass proportion of the porous carrier is preferably from 40 to 98% by mass, and more preferably from 50 to 95% by mass, based on the total mass of the catalyst. The porous carrier's proportion of not less than 40% by mass is favorable in that the metal element A can be dispersed. On the other hand, the porous carrier's proportion of not more than 98% by mass is favorable in that the conversion is improved.

[Oxide of Metal Element A]

The metal element A is at least one element selected from the group consisting of elements belonging to Groups 3 to 6 of the periodic table. At least a part of the oxide of the metal element A is bonded to the porous carrier.

The phrase "the oxide of the metal element A is bonded to the porous carrier" means that the metal element A and the porous carrier are chemically bonded (covalently bonded) to each other through an oxygen atom. In the bonding region, the metal element A and the oxygen atom are bonded to each other to produce an oxide of the metal element A.

Further, at least a part of each molecule of the oxide of the metal element A contained in the catalyst is bonded to the porous carrier. This allows the molecules of the oxide of the metal element A to be disposed close to the porous carrier (disposed inside the catalyst), whereby the selectivity for the diene compound can be improved as described above. Further, since the oxide of the metal element A is dispersed in the catalyst, the selectivity for the diene compound can be improved. Whether or not at least a part of the oxide of the metal element A contained in the catalyst is bonded to the porous carrier can be determined by the UV-Vis measurement. Specifically, it is defined that the presence of the bond is confirmed by the presence of one peak obtained in the UV-vis measurement, which is ascribed to the metal element A, at a position at least 10 nm away from the peak ascribed to the oxide of the metal element A in the catalyst.

Examples of the metal element A include, but are not particularly limited to, Group 3 elements such as scandium (Sc), yttrium (Y), lanthanum (La), and cerium (Ce); Group 4 elements such as titanium (Ti), zirconium (Zr), and hafnium (Hf); Group 5 elements such as vanadium (V), niobium (Nb), and tantalum (Ta); and Group 6 elements such as chromium (Cr), molybdenum (Mo), and tungsten (W). Of these, Group 3 elements, Group 4 elements and Group 5 elements are preferable, Group 4 elements and Group 5 elements are more preferable, zirconium (Zr), hafnium (Hf), niobium (Nb) and tantalum (Ta) are even more preferable, zirconium (Zr), hafnium (Hf) and niobium (Nb) are particularly preferable, zirconium (Zr) and hafnium (Hf) are even more preferable, and hafnium (Hf) is most preferable.

One of the metal elements A described above may be used alone, or two or more thereof may be used in combination.

The molar amount of the metal element A is preferably 0.5 to 15 mol %, more preferably 1 to 13 mol %, and even more preferably 2 to 10 mol %, with the proviso that the sum of the molar ratio of the element X, the molar ratio of the metal element A, and the molar ratio of the metal element B in the catalyst is 100 mol %. When two or more different metal elements A are used in combination, the sum of the molar amounts thereof is preferably within in the above range.

The ratio of the number of moles of the metal element A to the number of moles of the element X (metal element A/element X) is preferably from 0.001 to 1, more preferably from 0.02 to 0.5, even more preferably 0.02 to 0.15, and particularly preferably 0.07 to 0.15. The molar ratio, metal element A/element X, of not less than 0.001 is favorable in that the conversion can be improved. On the other hand, the molar ratio, metal element A/element X, of not more than 1 is favorable in that the metal element A can be dispersed.

[Oxide of Metal Element B]

The metal element B is at least one element selected from the group consisting of elements belonging to Groups 2 and 7 to 12 of the periodic table. Generally, the oxide of the metal element B is bonded to the porous carrier or the metal element A. Therefore, in principle, the oxide of the metal element B is disposed on the outermost surface of the catalyst. In this context, the phrase "the oxide of the metal element B is bonded to the porous carrier" means that the metal element B and the porous carrier are chemically bonded (covalently bonded) through an oxygen atom. In the bonding region, the metal element B and the oxygen atom are bonded to each other to produce an oxide of the metal element B. Further, the phrase "the oxide of the metal element B is bonded to the metal element A" means that the metal element B and the metal element A are chemically bonded (covalently bonded) through an oxygen atom. In the bonding region, the metal element B and the oxygen atom are bonded to each other to produce an oxide of the metal element B.

Further, the oxide of the metal element B may be bonded to another oxide of the metal element B. That is, unlike the case of the oxide of the metal element A, the catalyst may have a morphology in which the bond between the oxide of the metal element B and another oxide of the metal element B is arranged toward the outermost surface. In this context, the phrase "the oxide of the metal element B be bonded to another oxide of the metal element B" means that the metal element B present in the outermost surface of the catalyst and another metal element B positioned at an inner part of the catalyst are chemically bonded (covalently bonded) through an oxygen atom. In the bonding region, the metal element B on the outermost surface side and the oxygen atom are bonded to each other to produce an oxide of the metal element B.

This allows, as described above, the oxide of the metal element B to be disposed, in principle, on the outermost surface of the catalyst, thereby enabling improvement of the conversion. Further, since at least a part of the oxide of the metal element B is bonded to the oxide of the metal element A so that these are positioned close to each other, the selectivity for the diene compound and the conversion can be improved.

Examples of the metal element B include, but are not particularly limited to, Group 2 elements such as magnesium (Mg), calcium (Ca), strontium (Sr), and barium (Ba); Group 7 elements such as manganese (Mn); Group 8 elements such as iron (Fe) and ruthenium (Ru); Group 9 elements such as cobalt (Co) and rhodium (Rh); Group 10 elements such as nickel (Ni), palladium (Pd) and platinum (Pt); Group 11 elements such as copper (Cu), silver (Ag), and gold (Au); and Group 12 elements such as zinc (Zn). Of these, magnesium (Mg), calcium (Ca), manganese (Mn), iron (Fe), cobalt (Co), nickel (Ni), copper (Cu), and zinc (Zn) are preferable, and zinc (Zn) is more preferable.

One of the metal elements B described above may be used alone, or two or more thereof may be used in combination.

The molar amount of the metal element B is preferably 0.2 to 30 mol %, more preferably 0.2 to 25 mol %, and even more preferably 0.3 to 20 mol %, with the proviso that the sum of the molar ratio of the element X, the molar ratio of the metal element A, and the molar ratio of the metal element B in the catalyst is 100 mol %. When two or more different metal elements B are used in combination, the sum of the molar amounts thereof is preferably within in the above range.

The ratio of the number of moles of the metal element B to the number of moles of the metal element A (metal element B/metal element A) is preferably from 0.1 to 10, more preferably from 0.1 to 5, even more preferably 0.2 to 1.8, even more preferably 0.4 to 1.8, particularly preferably 0.4 to 1.2, and most preferably 0.5 to 1.0. The ratio, metal element B/metal element A, of not less than 0.1 is favorable in that the conversion is improved. On the other hand, the ratio, metal element B/metal element A, of not more than 10 is favorable in that the selectivity for the diene compound is improved.

[Other Metal Elements]

The catalyst may contain a metal element (other metal element) other than the metal element A and the metal element B as long as the effect of the present invention is not impaired.

[Configuration of Catalyst]

As described above, the catalyst includes the porous carrier, the oxide of the metal element A, and the oxide of the metal element B. At least a part of the oxide of the metal element A is bonded to the porous carrier.

FIG. 1 is a schematic view of a catalyst according to one embodiment of the present invention. Hereinbelow, an example of the configuration of the catalyst of an embodiment thereof using silica as the porous carrier is specifically described with reference to FIG. 1.

In FIG. 1, "A" represents the metal element A, and "B" represents the metal element B. Further, "(a)" represents the catalyst components including the oxide of the metal element A and the oxide of the metal element B, and "(b)" represents a surface layer on the silica surface.

Silanol groups present on the silica surface are bonded to the metal element A via oxygen atoms. Further, the metal element A is bonded to the metal element B via an oxygen atom.

The metal elements A are bonded to each other via an oxygen atom and are aligned in a two-dimensional direction (planar direction parallel to the surface of the porous carrier). Since at least a part of the oxide of the metal element A is bonded to the porous carrier, the metal elements A are, in principle, not bonded to each other via an oxygen atom in a three-dimensional direction (thickness direction relative to the surface of the porous carrier). For this reason, the metal element A is dispersed in the catalyst, which allows for improvement of the selectivity for the diene compound.

On the other hand, as a modification of FIG. 1, the metal elements B may be bonded to each other via an oxygen atom and be aligned in a two-dimensional direction (planar direction parallel the surface of the porous carrier). Further, the metal elements B may be bonded to each other via an oxygen atom and be aligned in a three-dimensional direction (thickness direction relative to the surface of the porous carrier).

The amount of the supported catalyst components of the catalyst is preferably from 5 to 150 parts by mass, and more preferably from 10 to 100 parts by mass, with respect to 100 parts by mass of the porous carrier. When the amount of the supported catalyst components is 5 parts by mass or more, the amount is large enough to increase the conversion and the selectivity for the diene compound, which is favorable. On the other hand, when the amount of the supported catalyst components of the catalyst is 150 parts by mass or less, the oxide of the metal element A can be suitably dispersed, and the selectivity for the diene compound is further increased, which is preferable. In the present specification, the "catalyst components" means the oxide of the metal element A and the oxide of the metal element B. Further, in the present specification, the amount of the supported catalyst components is a value measured by inductively coupled plasma (ICP) fluorescence spectroscopy (ICP-AES).

The average pore diameter of the catalyst is preferably from 2 to 50 nm, more preferably from 2 to 30 nm, and even more preferably from 2 to 15 nm. The average pore diameter of not less than 2 nm is favorable in that the diffusibility of the raw material gas containing an alcohol is improved, and the raw material conversion and the selectivity for the diene compound are further increased. On the other hand, the average pore diameter of not more than 50 nm is favorable in that the contact area between the alcohol and the catalyst tends to be sufficient, and the raw material conversion and the selectivity for the diene compound are further increased.

The total pore volume of the catalyst (hereinafter, also referred to as the total pore volume) is preferably 0.10 to 8.00 mL/g. The total pore volume of not less than 0.10 mL/g is favorable in that the diffusivity of the raw material gas containing an alcohol is improved, and the raw material conversion and the selectivity for the diene compound are further increased. On the other hand, the total pore volume of not more than 8.00 mL/g is favorable in that the contact area between the alcohol and the catalyst tends to be sufficient, and the raw material conversion and the selectivity for the diene compound are further increased.

The specific surface area of the catalyst is preferably 50 to 3000 m$^2$/g, and more preferably 500 to 2000 m$^2$/g. The specific surface area of not less than 50 m$^2$/g is favorable in that a sufficient amount of active sites are provided on the catalyst surface, which allows for further increase in the raw material conversion and the selectivity for the diene compound. As a result, the raw material conversion is increased even when the alcohol content is high with respect to 100% by volume of the raw material gas (in terms of gas volume). For example, a high raw material conversion is achieved even with the alcohol content of 100% by volume. On the other hand, the specific surface area of not more than 3000 m$^2$/g is favorable in that the contact area between the alcohol and the catalyst increases, and the raw material conversion and the selectivity for the diene compound are further increased.

The product of the total pore volume times the specific surface area of the porous carrier is preferably 5 to 24000 mL·m$^2$/g$^2$, and more preferably 10 to 20000 mL·m$^2$/g$^2$. The product of not less than 5 mL·m$^2$/g$^2$ is favorable in that a sufficient amount of active sites are provided on the catalyst surface and the diffusivity of the raw material gas containing an alcohol is improved, thereby allowing for further increase in the raw material conversion and the selectivity for the diene compound. On the other hand, when the product is not more than 24000 mL·m$^2$/g$^2$, the contact area between the alcohol and the catalyst tends to be sufficient, and the raw material conversion and the selectivity for the diene compound are further increased.

The total mesopore volume ratio (total mesopore volume/total pore volume×100) of the catalyst is preferably 50% or more, more preferably 50 to 100%, even more preferably 80 to 100%, and particularly preferably 90 to 100%. The total mesopore volume ratio of 50% or more is favorable in that a sufficient amount of mesopores are provided in the catalyst and the diffusivity of the raw material gas containing an alcohol is improved, thereby allowing for further increase in the raw material conversion and the selectivity for the diene compound.

The catalyst described above is preferably used as a catalyst for synthesizing a diene compound from a raw material gas containing an alcohol.

<Method for Producing Catalyst>

The present invention in another aspect provides a method for producing the catalyst. The method includes: a step of reacting a compound containing the metal element A with the porous carrier to prepare a catalyst precursor in which at least a part of the oxide of the metal element A is bonded to the porous carrier (precursor preparation step); and a step of reacting the catalyst precursor with a compound containing the metal element B (catalyst formation step). In addition, the method may further include a step of preparing a porous carrier (porous carrier preparation step).

In one preferred embodiment, the method includes the porous carrier preparation step, the precursor preparation step, and the catalyst formation step, which are implemented in this order.

[Porous Carrier Preparation Step]

The porous carrier preparation step is a step of preparing a porous carrier containing at least one element X selected from the group consisting of elements belonging to Groups 13 and 14 of the periodic table.

A specific preparation method is not particularly limited, and a conventionally known method can be appropriately employed. In one example of such a method, from solids contained in a liquid mixture obtained by mixing a compound containing the element X, a surfactant, and a solvent containing water (hereinafter, also referred to as a "solvent for carrier"), the surfactant and the solvent for carrier are removed.

(Liquid Mixture)

The liquid mixture contains a compound containing the element X, a surfactant, and a solvent for carrier. In addition, if necessary, the liquid mixture may further contain an acidic aqueous solution, a basic aqueous solution and the like.

Compound Containing Element X

The compound containing the element X is not particularly limited. Examples thereof include inorganic salts such as chlorides, sulfides, nitrates, and carbonates; organic salts such as oxalate, acetylacetonate, dimethylglyoxime salt, and ethylenediamine acetate; chelate compounds; carbonyl compounds; cyclopentadienyl compounds; ammine complexes; alkoxide compounds; alkyl compounds; and the like. For example, as a compound containing Si, the following compounds can be listed as examples thereof: amorphous silica such as colloidal silica, fumed silica, and silica gel; alkali metal silicate compounds such as sodium silicate and potassium silicate; tetramethoxysilane; tetraethoxysilane; and the like.

Among these, it is preferable to use an alkoxide compound containing silicon.

Specifically, the alkoxide compound containing a silicon element is preferably a compound represented by the following formula 1:

                Formula 1 wherein each R$_1$ independently represents an alkyl group. The alkyl group is preferably an alkyl group having 1 to 4 carbon atoms, and more preferably an ethyl group.

Specific examples of the alkoxide compound containing silicon include tetramethoxysilane, tetraethoxysilane, tetrapropoxysilane and the like. Of these, it is preferable to use tetraethoxysilane.

One of the compounds containing the element X described above may be used alone, or two or more thereof may be used in combination.

The amount of the compound containing the element X to be used is preferably 0.20 to 20 parts by mass, and more preferably 2.0 to 20 parts by mass, with respect to 100 parts by mass of the solvent for carrier.

Surfactant

The use of a surfactant enables the production of a porous carrier having mesopores. More specifically, the addition of a surfactant produces micelles which serve as template to form a precursor on the surfaces thereof. By subjecting the precursor to a calcination as described below, the surfactant is removed and a porous carrier having mesopores can be produced. The shape of the micelles may be spherical, cylindrical, lamellar, gyroidal, or vesicle-like depending on the concentration of the surfactant.

The surfactant is not particularly limited and may be a cationic surfactant, a nonionic surfactant, etc.

Examples of the cationic surfactant include those conventionally used in the production of mesoporous silica, such as MCM-41, SBA-15, and FMS-16. Specific examples of the cationic surfactant include alkyl ammonium salts ($C_nH_{2n+1}N^+(CH_3)_3$, wherein n represents an integer of 1 or more), such as hexadecyltrimethylammonium chloride.

Examples of the nonionic surfactant include, but are not particularly limited to, a polyalkylene oxide block copolymer containing an alkylene oxide chain, and a compound in which the ends of the block copolymer is etherified with an alcohol, phenol, or the like. Specific examples of the nonionic surfactant include polyalkylene oxide block copolymers having a polyethylene oxide chain $(CH_2CH_2O)_m$ and a polypropylene oxide chain $(CH_2CH(CH_3)O)$ u as structural units, wherein m and n are 1 to 1000, preferably m is 1 to 200 and n is 1 to 100, more preferably m is 1 to 200 and n is 1 to 100, with the proviso that m+n is 2 to 300. The ends of the polymer may be a hydrogen atom, a hydroxyl group, or etherified with an alcohol or phenol. Further, the alkylene oxide chains included as structural units may be of one type or of two or more types.

Among the polyalkylene oxide block copolymers described above, it is preferable to use a polyethylene oxide-polypropylene oxide-polyethylene oxide copolymer from the viewpoint of the stability of the crystal structure of the pore walls forming the mesopores.

The amount of the surfactant to be used is preferably 1 to 10 parts by mass, more preferably 1 to 5 parts by mass, and even more preferably 1 to 3 parts by mass, with respect to 100 parts by mass of the solvent for carrier.

Solvent for Carrier

The solvent for carrier includes water. The solvent for carrier may further include an organic solvent.

The water is not particularly limited, but is preferably ion-exchanged water or distilled water from which metal ions and the like have been removed.

Examples of the organic solvent include, but are not particularly limited to, aliphatic linear alcohols such as methanol, ethanol, n-propanol and n-hexanol, and ethylene glycol.

Among these, the organic solvent is preferably methanol or ethanol from the viewpoint of handling.

One of the above organic solvents may be used alone, or two or more thereof may be used in combination.

The amount of water in the solvent for carrier is preferably 50 to 100% by mass, more preferably 60 to 100% by mass, and even more preferably 65 to 100% by mass, based on the total mass of the solvent for carrier.

The amount of the solvent for carrier is preferably 5 to 35 parts by mass, and more preferably 5 to 20 parts by mass, per 1 part by mass of the surfactant.

Acidic Aqueous Solution

The acidic solution has a function of accelerating the generation of solids through the hydrolysis described below.

The acidic solution is not particularly limited, and examples thereof include an aqueous solution in which an inorganic acid such as hydrogen chloride, sulfuric acid, nitric acid, or phosphoric acid is dissolved.

Basic Aqueous Solution

The basic solution has a function of accelerating the generation of solids through the hydrolysis described below. In general, one of the above-mentioned acidic aqueous solution and basic aqueous solution is used.

Examples of the basic solution include, but are not particularly limited to, an aqueous solution in which an inorganic base such as sodium hydroxide, calcium carbonate, or ammonia is dissolved.

The average pore diameter, total pore volume, specific surface area, product of the pore volume times the specific surface area, mesopore volume ratio, shape, crystal structure of the pore wall, etc. of the porous carrier can be controlled by appropriately selecting or adjusting the type, concentration, hydrolysis condition, etc. of the surfactant, the compound containing the element X, the organic solvent, etc.

(Removal of Surfactant and Solvent for Carrier)

The liquid mixture contains the compound containing the element X, the surfactant, and water. As a result, the compound containing the element X is hydrolyzed and condensed to generate solids. Then, a porous carrier having mesopores can be produced by removing the surfactant and the solvent for carrier from the solids.

Examples of the method for removing the surfactant include a method of washing with water or an organic solvent such as toluene, methanol, ethanol, or acetone; a method of washing with an acidic aqueous solution such as hydrochloric acid, or an aqueous solution of sulfuric acid or nitric acid; a heat treatment (for example, at 200 to 800° C.).

Examples of the method for removing the solvent for carrier include a filtration method; a heat treatment (at 20 to 1000° C.); and a natural drying method.

The method for removing the surfactant and the method for removing the solvent for carrier may be performed individually or in combination. Further, the treatment conditions may be appropriately changed.

[Precursor Preparation Step]

The precursor preparation step is a step of reacting a compound containing the metal element A with the porous carrier to prepare a catalyst precursor in which at least a part of the oxide of the metal element A is bonded to the porous carrier.

The method for preparing the catalyst precursor is not particularly limited, but is preferably a method including: a step of impregnating a porous carrier with a first solution containing a compound containing the metal element A to obtain a solution containing an impregnated product (impregnated product-containing solution preparation step); a step of separating the impregnated product from the first solution (impregnated product separation step); and a step of calcining the impregnated product (first calcination step). Hereinbelow, an embodiment of the method is described in detail.

(Impregnated Product-Containing Solution Preparation Step)

The impregnated product-containing solution preparation step is a step of impregnating the porous carrier with the first solution containing the compound containing the metal element A to obtain a solution containing the impregnated product.

First Solution

The first solution contains a compound containing the metal element A. In addition, the first solution may further contain a solvent as necessary.

The compound containing the metal element A is not particularly limited. Examples thereof include inorganic salts such as chlorides, sulfides, nitrates and carbonates; organic salts or chelate compounds such as oxalates, acetylacetonate salts, dimethylglyoxime salts and ethylenediamine acetic acid salts; carbonyl compounds; cyclopentadienyl compounds; ammine complexes; alkoxide compounds; and alkyl compounds.

Specific examples include titanium chloride ($TiCl_2$, $TiCl_3$, $TiCl_4$), zirconium chloride ($ZrCl_2$), hafnium chloride ($HfCl_4$), niobium chloride ($NbCl_5$), tantalum chloride ($TaCl_5$), vanadium chloride ($VCl_3$), tungsten chloride ($WCl_5$), scandium nitrate ($Sc(NO_3)_3$), yttrium nitrate ($Y(NO_3)_3$), lanthanum nitrate ($La(NO_3)_3$), and cerium nitrate ($Ce(NO_3)_3$). Among these, one of the compounds containing the element A described above may be used alone, or two or more thereof may be used in combination.

The molar amount of the compound containing the metal element A may be 0.5 to 40 mol %, more preferably 1 to 20 mol %, and even more preferably 2 to 15 mol %, with the proviso that the sum of the molar ratio of the element X, the molar ratio of the compound containing the metal element A, and the molar ratio of the compound containing the metal element B described below in the porous carrier is 100 mol %. When two or more different metal elements A are used in combination, the sum of the molar amounts thereof is preferably within in the above range.

The ratio of the number of moles of the compound containing the metal element A to the number of moles of the element X in the porous carrier (compound containing metal element A/element X) is preferably from 0.001 to 2, more preferably from 0.02 to 1, even more preferably 0.02 to 0.5, and particularly preferably 0.07 to 0.5. The molar ratio, compound containing metal element A/element X, of not less than 0.001 is favorable in that the conversion can be improved. On the other hand, the molar ratio, compound containing metal element A/element X, of not more than 2 is favorable in that the metal element A can be dispersed.

Examples of the solvent include water; and organic solvents such as methanol, ethanol, tetrahydrofuran, dioxane, hexane, benzene, and toluene. One of these solvents may be used alone, or two or more of these may be used in combination.

The amount of the first solution to be used is preferably 1000 to 10000 parts by mass, more preferably 3000 to 7000 parts by mass, and even more preferably 4000 to 6000 parts by mass, with respect to 100 parts by mass of the porous carrier.

The amount of the first solution within the above range is favorable in that the compound containing the metal element A is uniformly distributed in the pores of the porous carrier, which allows the metal element A to be dispersed.

Porous Carrier

The porous carrier to be used is as described above and therefore detailed descriptions are omitted here.

Impregnation

The impregnation is implemented by impregnating the porous carrier with the first solution.

The impregnation time is preferably from 30 minutes to 20 hours, more preferably from 1 to 14 hours, and even more preferably from 3 to 10 hours. The impregnation time of not less than 30 minutes is favorable in that a sufficient amount of the oxide of the metal element A can be supported on the porous carrier. On the other hand, the impregnation time of not more than 20 hours is favorable in that aggregation of the metal element A can be suppressed or prevented.

As a result of the impregnation, a solution containing the impregnated product can be obtained. The compound containing the metal element A is dissolved in the solution containing the impregnated product.

(Impregnated Product Separation Step)

The impregnated product separation step is a step of separating the impregnated product from the first solution in the solution containing the impregnated product. The impregnated product obtained by the impregnated product separation step has a configuration in which the compound containing the metal element A is attached to the porous carrier. On the other hand, in the separated first solution, the compound containing the metal element A is dissolved. That is, as a result of the impregnated product separation step, only the compound containing the metal element A attached to the porous carrier is allowed to react when the obtained impregnated product is subjected to the first calcination step described later. In other words, when the compound containing the metal element A reacts with the porous carrier in the first calcination step described later, the compound containing the metal element A does not exist in the first solution, whereby the compound containing the metal element A capable of reacting with the porous carrier is limited to those attached to the porous carrier. As a consequence, in the obtained catalyst precursor, at least a part of the oxide of the metal element A is bonded to the porous carrier.

Examples of a method for separating the impregnated product from the first solution include filtration, centrifugation, pipetting, and the like. A method such as solvent distillation is not generally adopted because only the solvent is distilled off and an excess amount of the compound containing the metal element A cannot be removed.

The impregnated product obtained in the impregnated product separation step is preferably washed with a solvent and dried if necessary.

(First Calcination Step)

The first calcination step is a step of calcining the impregnated product.

The calcination of the impregnated product allows the porous carrier and the compound containing the metal element A to react with each other, which enables the preparation of a catalyst precursor in which at least a part of the oxide of the metal element A is bonded to the porous carrier.

The calcination temperature is preferably from 200 to 800° C., more preferably from 300 to 700° C., and even more preferably from 400 to 600° C. The calcination temperature of not lower than 200° C. is favorable in that the oxide of the metal element A can be formed uniformly on the surface of the porous carrier. On the other hand, the calcination temperature of not higher than 800° C. is favorable in that a decrease in the specific surface area of the obtained catalyst can be prevented or suppressed.

The calcination time is preferably 1 to 20 hours, more preferably 3 to 14 hours, and even more preferably 5 to 10 hours. The calcination time of not less than 1 hour is favorable in that the oxide of the metal element A can be formed uniformly on the surface of the porous carrier. On the other hand, the calcination time of not more than 20 hours is favorable in that a decrease in the specific surface area of the obtained catalyst can be prevented or suppressed.

The calcination atmosphere is not particularly limited, and may be air or an inert gas.

[Catalyst Formation Step]

The catalyst formation step is a step of reacting the catalyst precursor with a compound containing the metal element B.

The catalyst formation step preferably includes a step of contacting the catalyst precursor with the compound containing the metal element B (contact step), and a step of calcining the resulting contacted product (second calcination step).

(Contact Step)

The contact step is a step of bringing the catalyst precursor into contact with the compound containing the metal element B.

The catalyst precursor to be used is as described above.

The compound containing the metal element B is not particularly limited. Examples thereof include inorganic salts such as chlorides, sulfides, nitrates and carbonates; organic salts or chelate compounds such as oxalates, acetylacetonate salts, dimethylglyoxime salts and ethylenediamine acetic acid salts; carbonyl compounds; cyclopentadienyl compounds; ammine complexes; alkoxide compounds; and alkyl compounds.

Specific examples include magnesium chloride ($MgCl_2$), calcium chloride ($CaCl_2$)), iron chloride, ($FeCl_2$, $FeCl_3$), nickel nitrate ($NiNO_3$), zinc chloride ($ZnCl_2$), zinc nitrate ($Zn(NO_3)_2$), copper nitrate ($Cu(NO_3)_2$), and copper chloride ($CuCl_2$).

One of the compounds containing the element B described above may be used alone, or two or more thereof may be used in combination.

The molar amount of the compound containing the metal element B may be 0.2 to 30 mol %, more preferably 0.2 to 25 mol %, and even more preferably 0.3 to 20 mol %, with the proviso that the sum of the molar ratio of the element X, the molar ratio of the metal element A, and the molar ratio of the metal element B in the catalyst is 100 mol %. When two or more different metal elements B are used in combination, the sum of the molar amounts thereof is preferably within in the above range.

The ratio of the number of moles of the compound containing the metal element B to the number of moles of the compound containing the metal element A (compound containing metal element B/compound containing metal element A) is preferably 0.1 to 10, more preferably 0.1 to 5, more preferably 0.2 to 1.8, even more preferably 0.4 to 1.8, particularly preferably 0.4 to 1.2, and most preferably 0.4 to 1.0.

The contact between the catalyst precursor and the compound containing the metal element B can be performed by a known method. Examples of the method include a method of impregnating the catalyst precursor with a second solution containing the compound containing the metal element B; a method of applying the second solution to or dropping the second solution on the catalyst precursor; and a method of spraying the compound containing the metal element B to the catalyst precursor.

Examples of the solvent used in the second solution include water; and organic solvents such as methanol, ethanol, tetrahydrofuran, dioxane, hexane, benzene, and toluene. One of these solvents may be used alone, or two or more of these may be used in combination.

The amount of the second impregnation solution to be used is preferably 1000 to 10000 parts by mass, more preferably 3000 to 7000 parts by mass, and even more preferably 4000 to 6000 parts by mass, with respect to 100 parts by mass of the catalyst precursor.

When the contact is implemented using a solvent, it is preferable to remove the solvent appropriately to obtain the contacted product.

(Second Calcination Step)

The second calcination step is a step of calcining the contacted product.

That is, the compound containing the metal element B is in contact with the catalyst precursor. The calcination of the contacted product allows the compound containing the metal element B to react with the porous carrier forming the catalyst precursor or the oxide of the metal element A, thereby producing the catalyst.

The calcination temperature is preferably from 300 to 600° C., more preferably from 350 to 550° C., and even more preferably from 375 to 500° C. The calcination temperature of not lower than 300° C. is favorable in that the oxide of the metal element B can be uniformly formed. On the other hand, the calcination temperature of not higher than 600° C. is favorable in that aggregation of the metal element B can be prevented.

The calcination time is preferably 1 to 20 hours, more preferably 3 to 14 hours, and even more preferably 5 to 10 hours. The calcination time of not less than 1 hour is favorable in that the oxide of the metal element B can be formed uniformly. On the other hand, the calcination time of not more than 20 hours is favorable in that aggregation of the metal element B can be prevented.

The calcination atmosphere is not particularly limited, and may be air or an inert gas.

<Apparatus for Producing Diene Compound>

The apparatus for producing a diene compound includes a reaction tube filled with the catalyst described above. The apparatus is used for producing a diene compound from a raw material gas containing a raw material.

Hereinbelow, a butadiene production apparatus, which is one type of the apparatus for producing a diene compound, is described with reference to FIG. 1.

The butadiene production apparatus 10 of the present embodiment (hereinafter, simply referred to as "production apparatus 10") includes a reaction tube 1, a supply pipe 3, a outlet pipe 4, a temperature controller 5, and a pressure controller 6.

The reaction tube 1 has a reaction bed 2 inside. The reaction bed 2 is packed with the synthesis catalyst of the present invention. The supply pipe 3 is connected to the reaction tube 1. The outlet pipe 4 is connected to the reaction tube 1. The temperature controller 5 is connected to the reaction tube 1. The outlet pipe 4 is equipped with the pressure controller 6.

The reaction bed 2 may have only the catalyst of the present invention, or may have another catalyst as well as the catalyst of the present invention. Further, the reaction bed 2 may also contain a diluent. The diluent prevents the catalyst from generating excessive heat.

Here, the reaction for synthesizing butadiene from the raw material is an endothermic reaction. For this reason, the reaction bed 2 usually does not require a diluent.

The diluent may be, for example, quartz sand, alumina balls, aluminum balls, aluminum shots, and the like.

When a diluent is charged into the reaction bed 2, the mass ratio, diluent/synthesis catalyst, is determined in consideration of the type, specific gravity, and the like of the diluent and the synthesis catalyst, and is, for example, preferably 0.5 to 5. The reaction bed may be any of a fixed bed, a moving bed, a fluidized bed, and the like.

The reaction tube 1 is preferably made of a material that is inert to the raw material gas and the synthesized product. The reaction tube 1 preferably has a shape that enables the reaction tube 1 to withstand heating at about 100 to 500° C. or pressurization at about 10 MPa. The reaction tube 1 may be, for example, a substantially cylindrical member made of stainless steel.

The supply pipe 3 is a supply means that supplies the raw material gas into the reaction pipe 1. The supply pipe 3 is, for example, a pipe made of stainless steel.

The outlet pipe 4 is an outlet means that releases a gas containing a product synthesized in the reaction bed 2. The outlet pipe 4 is, for example, a pipe made of stainless steel or the like.

With respect to the temperature controller 5, there is no particular limitation as long as it can control the temperature of the reaction bed 2 in the reaction tube 1 to a desired value. For example, the temperature controller 5 may be an electric furnace or the like.

With respect to the pressure controller 6, there is no particular limitation as long as it can control the internal pressure of the reaction tube 1 to a desired value. For example, the pressure controller 6 may be a known pressure valve or the like.

The production apparatus 10 may be equipped with a known device such as a gas flow rate controller (e.g., mass flow controller) or the like which adjusts a flow rate of the gas.

<Method for Producing Diene Compound>

The present invention in one aspect thereof provides a method for producing a diene compound. The method for producing a diene compound includes contacting a raw material gas containing an alcohol with the catalyst of the present invention to thereby produce a diene compound.

[Catalyst]

The catalyst to be used is as described above and therefore detailed descriptions are omitted here.

The amount of the catalyst to be used is preferably 0.1 to 10 g/g·h, and more preferably 1 to 5 g/g·h, based on the amount of the raw material gas. The catalyst amount of not less than 0.1 g/g·h is favorable in that the reaction conversion can be improved. On the other hand, the catalyst amount of not more than 10 g/g·h is favorable in that generation of by-products can be suppressed.

[Raw Material Gas]

The raw material gas contains an alcohol. In addition, the raw material gas may further include an aldehyde, an inert gas, and the like.

(Alcohol)

Examples of the alcohol include, but are not particularly limited to, alcohols having 1 to 6 carbon atoms. Specific examples of the alcohol include methanol, ethanol, propanol, butanol, pentanol, hexanol and the like.

In principle, the diene compound to be obtained depends on the type of alcohol used. For example, when ethanol is used, butadiene is obtained. When propanol is used, hexadiene is obtained. When butanol is used, octadiene is obtained.

The alcohol used may be of a single type or a mixture of two or more types, but is preferably of a single type from the viewpoint of suppressing side reactions.

The concentration of the alcohol in the raw material gas is preferably 10% by volume or more, more preferably 15% by volume or more, even more preferably 20% by volume or more, even more preferably at least 30% by volume, particularly preferably 50% by volume or more, and most preferably from 75% by volume or more, with respect to 100% by volume of the raw material gas. When two or more different alcohols are used in combination, the sum of the amounts thereof is preferably within in the above range. The use of the catalyst according to the present invention enables the reaction to proceed efficiently even when the alcohol concentration in the raw material gas is high.

(Aldehyde)

Aldehydes are usually oxides of alcohols. Specific examples thereof include formaldehyde, acetaldehyde, propionaldehyde, butyraldehyde, valeraldehyde, and the like.

When the raw material gas contains an aldehyde, the aldehyde is generally one corresponding to the alcohol. Specifically, when methanol is used as the alcohol, the aldehyde is formaldehyde. Likewise, the aldehyde is acetaldehyde when using ethanol as the alcohol, the aldehyde is propionaldehyde when using propanol as the alcohol, the aldehyde is butyraldehyde when using butanol as the alcohol, and the aldehyde is valeraldehyde when using pentanol as the alcohol. However, the aldehyde may include an aldehyde other than the aldehyde corresponding to the alcohol.

The concentration of the aldehyde in the raw material gas is preferably 1% by volume or more, more preferably 5% by volume or more, even more preferably 10% by volume or more, particularly preferably at least 50% by volume, and most preferably from 75 to 99% by volume, with respect to 100% by volume of the raw material gas. When two or more different alcohols are used in combination, the sum of the amounts thereof is preferably within in the above range.

The total concentration of the alcohol and the aldehyde in the raw material gas is preferably 15% by volume or more, more preferably 20% by volume or more, and even more preferably from 20 to 40% by volume, with respect to 100% by volume of the raw material gas.

(Inert Gas)

Examples of the inert gas include, but are not particularly limited to, nitrogen gas and argon gas. One of these inert gases may be used alone or two or more of these may be used in combination.

The concentration of the inert gas is preferably 90% by volume or less, more preferably 30 to 90% by volume, even more preferably 50 to 90% by volume, and particularly preferably 60 to 80% by volume, with respect to 100% by volume of the raw material gas.

[Contacting]

With respect to the method for bringing the raw material gas into contact with the catalyst, there is no particular limitation. A preferred example thereof is a method in which the raw material gas is passed through the reaction bed in the reaction tube so as to allow the synthesis catalyst in the reaction bed to contact the raw material gas.

The temperature (reaction temperature) at which the catalyst is brought into contact with the raw material gas is preferably from 100 to 600° C., more preferably from 200 to 600° C., even more preferably from 200 to 450° C., particularly preferably from 200 to 370° C., and most preferably from 250 to 360° C. The reaction temperature of not lower than 100° C. is favorable in that the reaction rate is sufficiently increased, and the diene compound can be produced more efficiently. On the other hand, the reaction temperature of not higher than 600° C. is favorable in that deterioration of the catalyst can be prevented or suppressed.

The pressure (reaction pressure) at which the raw material gas is brought into contact with the catalyst is preferably 0.1 to 10 MPa, and more preferably 0.1 to 3 MPa. The reaction pressure of not less than 0.1 MPa is favorable in that the reaction rate is increased, and the diene compound can be produced more efficiently. On the other hand, the reaction pressure of not more than 10 MPa is favorable in that deterioration of the catalyst can be prevented or suppressed.

The space velocity (SV) of the raw material gas in the reaction bed is usually adjusted appropriately in consideration of the reaction pressure and the reaction temperature, but is preferably 0.1 to 10000 $h^{-1}$ in terms of the value under the standard condition.

For example, when butadiene is produced using the production apparatus 10, the temperature controller 5 and the pressure controller 6 adjust the internal temperature and pressure of the reaction tube 1 to the respective predetermined values. The raw material gas 20 is supplied from the supply pipe 3 into the reaction tube 1. In the reaction tube 1, the raw material comes into contact with the synthesis catalyst and reacts to generate butadiene. The product gas 22 containing butadiene is released from the outlet pipe 4. The product gas 22 may contain compounds such as acetaldehyde, propylene, and ethylene.

With respect to the product gas containing the diene compound (product gas 22 in FIG. 1), the product gas is subjected to purification such as gas-liquid separation or distillation purification as necessary to remove unreacted raw materials and by-products. The present invention also enables the production of a diene compound from bioethanol to thereby reduce the environmental burden.

EXAMPLES

Hereinbelow, the present invention will be described with reference to Examples which, however, should not be construed as limiting the present invention.

Example 1

[Preparation of Mesoporous Silica]
4 g of P123 ([(HO(CH$_2$CH$_2$O)$_{20}$(CH$_2$CH(CH$_3$)O)$_{70}$(CH$_2$CH$_2$O)$_{20}$)H], manufactured by BASF) as a surfactant and 8.5 g of tetraethoxysilane were charged into a beaker, followed by addition of 150 g of a 2 mol/L hydrochloric acid aqueous solution, and the resulting was stirred at room temperature for 20 hours to carry out hydrolysis.

The solids in the solution after hydrolysis were separated by filtration, and dried at 30° C. for 6 hours in an air atmosphere.

The dried solids were calcined in an electric furnace under an air atmosphere at 500° C. for 14 hours to obtain a mesoporous silica.
[Production of Catalyst]
0.6 g of hafnium chloride (HfCl$_4$) was dissolved in 100 g of water to obtain a first impregnation solution. 2.0 g of the mesoporous silica (average pore diameter: 2.8 nm, total pore volume: 1.09 mL/g, specific surface area: 995 m$^2$/g) was added to the first impregnation solution, and the resulting mixture was stirred at room temperature for 4 hours to perform impregnation. The mesoporous silica after impregnation was separated from the solution containing hafnium chloride by suction filtration, and was dried at 80° C. for 4 hours in an air atmosphere, thereby obtaining an impregnated product.

The impregnated product was calcined at 400° C. for 6 hours to obtain a catalyst precursor in which an oxide of hafnium oxide was supported on the mesoporous silica (a silicon atom and a hafnium atom were bonded via an oxygen atom).

1.0 g of zinc nitrate hexahydrate (Zn(NO$_3$)$_2$·6H$_2$O) was dissolved in 100 g of water to obtain a second impregnation solution. The second impregnation solution was added dropwise to the catalyst precursor. The resulting was dried at 80° C. for 4 hours, followed by calcination at 400° C. for 6 hours in an electric furnace under an air atmosphere to produce a catalyst.

The molar amounts (mol %) of Hf and Zn in the obtained catalyst were measured by the following method. That is, a certain amount of the obtained catalyst was weighed, decomposed by alkali melting, dissolved in an acid, and the volume of the resulting solution was fixed to obtain a test solution. The molar amounts (mol %) of Hf and Zn in the test solution were measured by an ICP emission spectrometer. As a result, the molar amount of Hf was found to be 0.97 mol %, and the molar amount of Zn was found to be 1.96 mol %. Further, the molar amount of Si (mol %) is a value obtained by subtracting the Hf molar amount and the Zn molar amount from 100. Therefore, the molar amount of Si in the catalyst is 97.07 mol %.

Further, with respect to the obtained catalyst, the results of the UV-vis measurement confirmed that at least a part of the oxide of Hf was bonded to mesoporous silica. In the measurement, only one peak was observed at 234 nm.

The results are shown in Table 1.

Example 2

A catalyst was produced in the same manner as in Example 1, except that the amounts of tetraethoxysilane, hafnium (IV) chloride, and zinc nitrate hexahydrate were adjusted so that the molar amounts of Hf and Zn in the catalyst were as shown in Table 1.

The molar amounts of Hf, Zn and Si were measured in the same manner as in Example 1 and found to be 4.37 mol %, 8.76 mol %, and 86.87 mol %, respectively.

Further, it was confirmed in the same manner as in Example 1 that at least a part of the oxide of Hf was bonded to the mesoporous silica.

The results are shown in Table 1.

Example 3

A catalyst was produced in the same manner as in Example 1, except that the amounts of tetraethoxysilane, hafnium (IV) chloride, and zinc nitrate hexahydrate were adjusted so that the molar amounts of Hf and Zn in the catalyst were as shown in Table 1.

The molar amounts of Hf, Zn and Si were measured in the same manner as in Example 1 and found to be 7.74 mol %, 15.5 mol %, and 76.76 mol %, respectively.

Further, it was confirmed in the same manner as in Example 1 that at least a part of the oxide of Hf was bonded to the mesoporous silica.

The results are shown in Table 1.

Example 4

A catalyst was produced in the same manner as in Example 1, except that the amounts of tetraethoxysilane, hafnium (IV) chloride, and zinc nitrate hexahydrate were adjusted so that the molar amounts of Hf and Zn in the catalyst were as shown in Table 1.

The molar amounts of Hf, Zn and Si were measured in the same manner as in Example 1 and found to be 12.5 mol %, 25.2 mol %, and 62.3 mol %, respectively.

Further, it was confirmed in the same manner as in Example 1 that at least a part of the oxide of Hf was bonded to the mesoporous silica.

The results are shown in Table 1.

Example 5

A catalyst was produced in the same manner as in Example 1, except that the amounts of tetraethoxysilane, hafnium (IV) chloride, and zinc nitrate hexahydrate were adjusted so that the molar amounts of Hf and Zn in the catalyst were as shown in Table 1.

The molar amounts of Hf, Zn and Si were measured in the same manner as in Example 1 and found to be 2.82 mol %, 20.9 mol %, and 76.28 mol %, respectively.

Further, it was confirmed in the same manner as in Example 1 that at least a part of the oxide of Hf was bonded to the mesoporous silica.

The results are shown in Table 1.

Example 6

A catalyst was produced in the same manner as in Example 1, except that the amounts of tetraethoxysilane, hafnium (IV) chloride, and zinc nitrate hexahydrate were adjusted so that the molar amounts of Hf and Zn in the catalyst were as shown in Table 1.

The molar amounts of Hf, Zn and Si were measured in the same manner as in Example 1 and found to be 3.24 mol %, 8.87 mol %, and 87.89 mol %, respectively.

Further, it was confirmed in the same manner as in Example 1 that at least a part of the oxide of Hf was bonded to the mesoporous silica.

The results are shown in Table 1.

Example 7

A catalyst was produced in the same manner as in Example 1, except that the amounts of tetraethoxysilane, hafnium (IV) chloride, and zinc nitrate hexahydrate were adjusted so that the molar amounts of Hf and Zn in the catalyst were as shown in Table 1.

The molar amounts of Hf, Zn and Si were measured in the same manner as in Example 1 and found to be 3.47 mol %, 2.59 mol %, and 93.94 mol %, respectively.

Further, it was confirmed in the same manner as in Example 1 that at least a part of the oxide of Hf was bonded to the mesoporous silica.

The results are shown in Table 1.

Example 8

A catalyst was produced in the same manner as in Example 1, except that the amounts of tetraethoxysilane, hafnium (IV) chloride, and zinc nitrate hexahydrate were adjusted so that the molar amounts of Hf and Zn in the catalyst were as shown in Table 1.

The molar amounts of Hf, Zn and Si were measured in the same manner as in Example 1 and found to be 3.52 mol %, 1.30 mol %, and 95.18 mol %, respectively.

Further, it was confirmed in the same manner as in Example 1 that at least a part of the oxide of Hf was bonded to the mesoporous silica.

The results are shown in Table 1.

Example 9

A catalyst was produced in the same manner as in Example 1, except that the amounts of tetraethoxysilane, hafnium (IV) chloride, and zinc nitrate hexahydrate were adjusted so that the molar amounts of Hf and Zn in the catalyst were as shown in Table 1.

The molar amounts of Hf, Zn and Si were measured in the same manner as in Example 1 and found to be 3.47 mol %, 2.58 mol %, and 93.95 mol %, respectively.

Further, it was confirmed in the same manner as in Example 1 that at least a part of the oxide of Hf was bonded to the mesoporous silica.

The results are shown in Table 1.

Example 10

A catalyst was produced in the same manner as in Example 1, except that the amounts of tetraethoxysilane, hafnium (IV) chloride, and zinc nitrate hexahydrate were adjusted so that the molar amounts of Hf and Zn in the catalyst were as shown in Table 1.

The molar amounts of Hf, Zn and Si were measured in the same manner as in Example 1 and found to be 3.47 mol %, 2.58 mol %, and 93.95 mol %, respectively.

Further, it was confirmed in the same manner as in Example 1 that at least a part of the oxide of Hf was bonded to the mesoporous silica.

The results are shown in Table 1.

Comparative Example 1

A catalyst was produced in the same manner as in Example 1 except that the porous carrier was changed to a commercially available silica (silica, particle diameter: 1.18 to 2.36 mm, average pore diameter: 10 nm, total pore volume: 1.01 mL/g, specific surface area: 283 m$^2$/g).

The molar amounts of Hf, Zn and Si were measured in the same manner as in Example 1 and found to be 3.47 mol %, 2.58 mol %, and 93.95 mol %, respectively.

Further, the UV-Vis measurement was performed in the same manner as in Example 1, and the results confirmed the presence of an oxide of Hf not bonded to the mesoporous silica. Specifically, peaks were observed at 211 nm and 234 nm. The results are shown in Table 1.

[Results of Evaluation]

Using the catalysts produced in Examples 1 to 10 and Comparative Example 1, a reaction was performed to produce 1,3-butadien from ethanol to determine the 1,3-butadiene (BD) selectivity, conversion, and yield of 1,3-butadiene (BD).

Specifically, 3.4 g of the catalyst was filled into a cylindrical reaction tube made of stainless steel and having a diameter of ½ inch (1.27 cm) and a length of 15.7 inch (40 cm) to form a reaction bed. Next, the reaction temperature (reaction bed temperature) was set to 350° C., 375° C., or 400° C., and the reaction pressure (reaction bed pressure) was set to 0.1 MPa. A raw material gas was supplied to the reaction tube at an SV of 1200 L/hr/catalyst amount (L-catalyst) to obtain a product gas. The raw material gas was a mixed gas of 30% by volume (in terms of gas volume) of ethanol and 70% by volume (in terms of gas volume) of nitrogen.

The recovered product gas was analyzed by gas chromatography to determine the BD selectivity, conversion, and BD yield ([conversion]×[BD selectivity]). The "BD selectivity" means a percentage of the number of moles of the raw material converted to butadiene out of the number of moles of the raw material consumed in the reaction using the catalyst. The "conversion (raw material conversion)" means a percentage of the number of moles consumed out of the number of moles of the raw material contained in the raw material gas.

The results are shown in Table 1.

TABLE 1

| | Metal element A | | Metal element B | | | Evaluation | | |
|---|---|---|---|---|---|---|---|---|
| | Type | Hf/Si ratio (molar ratio) | Type | Zn/Hf (molar ratio) | Reaction temperature (°C.) | BD selectivity (%) | Conversion (%) | BD yield (%) |
| Ex.1 | Hf | 0.01 | Zn | 2 | 350 | 29.2 | 65.6 | 19.2 |
| Ex.2 | Hf | 0.05 | Zn | 2 | 350 | 46.3 | 70.4 | 32.6 |
| Ex.3 | Hf | 0.1 | Zn | 2 | 350 | 45.8 | 73.7 | 33.8 |
| Ex.4 | Hf | 0.2 | Zn | 2 | 350 | 29.7 | 76.2 | 22.6 |
| Ex.5 | Hf | 0.04 | Zn | 7.4 | 350 | 46.8 | 81.9 | 38.3 |
| Ex.6 | Hf | 0.04 | Zn | 2.7 | 350 | 50.1 | 70.6 | 35.4 |
| Ex.7 | Hf | 0.04 | Zn | 0.74 | 350 | 61 | 69.1 | 42.1 |
| Ex.8 | Hf | 0.04 | Zn | 0.37 | 350 | 59.8 | 67.4 | 40.3 |
| Exx.9 | Hf | 0.04 | Zn | 0.74 | 375 | 39.8 | 76.2 | 30.3 |
| Ex.10 | Hf | 0.04 | Zn | 0.74 | 400 | 39.6 | 94 | 37.2 |
| Comp.Ex.1 | Hf | 0.04 | Zn | 0.74 | 350 | 20.4 | 57.3 | 11.7 |

The results show that the catalysts of Examples 1 to 10 can be suitably used to obtain 1,3-butadiene even when a large amount of ethanol is contained in the raw material gas.

DESCRIPTION OF THE REFERENCE SIGNS

1 Reaction tube
2 Reaction bed
3 Supply pipe
4 Outlet pie
5 Temperature controller
6 Pressure controller
10 Butadiene production apparatus

The invention claimed is:

1. A catalyst comprising:
    a porous carrier comprising at least one element X selected from the group consisting of elements belonging to Groups 13 and 14 of the periodic table; and
    an oxide of at least one metal element A selected from the group consisting of elements belonging to Groups 3 to 6 of the periodic table,
    wherein at least a part of the oxide of the metal element A is bonded to the porous carrier, and
    wherein the catalyst, in a UV-vis measurement, shows a single peak ascribed to the at least one metal element A at a wavelength position at least 10 nm away from a wavelength position where a peak ascribed to an oxide of the at least one metal element A is supposed to be found, while not showing a peak ascribed to the oxide of the at least one metal element A, and
    wherein the catalyst is produced by a process comprising a step of separating an impregnated product of the catalyst from a solution by a means for impregnated product separation.

2. The catalyst according to claim 1, wherein a ratio of the number of moles of the at least one metal element A to the number of moles of the at least one element X (metal element A/element X) is 0.001 to 1.

3. The catalyst according to claim 1, wherein the porous carrier has mesopores.

4. A method for producing the catalyst of claim 1, comprising:
    impregnating the porous carrier with a first solution containing a compound containing the at least one metal element A to obtain a solution containing an impregnated product;
    separating the impregnated product from the first solution by a means for impregnated product separation; and
    calcining the impregnated product.

5. The method according to claim 4, wherein the specific surface area of the porous carrier is 500 to 2000 m$^2$/g.

6. A method for producing a diene compound, comprising contacting the catalyst of claim 1 with a raw material gas containing an alcohol to obtain a diene compound.

7. The method according to claim 6, wherein a reaction temperature for obtaining the diene compound is 200 to 600° C.

8. The method according to claim 6, wherein the raw material gas is ethanol, or a mixture of ethanol and acetaldehyde.

9. The catalyst according to claim 1, further comprising at least one oxide of a metal element B selected from the group consisting of elements belonging to Group 2 and Groups 7 to 12 of the periodic table.

10. The catalyst according to claim 9, wherein a ratio of the number of moles of the metal element B to the number of moles of the at least one element A (metal element B/element A) is 0.1 to 10.

* * * * *